United States Patent
Chien et al.

(10) Patent No.: US 8,859,246 B2
(45) Date of Patent: Oct. 14, 2014

(54) **METHOD TO PRODUCE PHBV BY RECOMBINANT *ESCHERICHIA COLI***

(75) Inventors: Chih-Ching Chien, Hsinchu (TW); Po-Chi Soo, Taipei (TW); Yu-Tze Horng, Taipei (TW); Shan-Yu Chen, Chiayi (TW); Hsiu-Hsiung Li, Chung-Li (TW); Yu-Hong Wei, Chung-Li (TW); Wen-Ming Chen, Chung-Li (TW)

(73) Assignee: Yuan Ze University, Chung-Li (TW)

( * ) Notice: Subject to any disclaimer, the term of this patent is extended or adjusted under 35 U.S.C. 154(b) by 0 days.

(21) Appl. No.: 13/482,422

(22) Filed: May 29, 2012

(65) Prior Publication Data

US 2013/0323804 A1  Dec. 5, 2013

(51) Int. Cl.
*C12P 7/62* (2006.01)
*C12P 19/34* (2006.01)
*C12N 15/00* (2006.01)
*C12N 1/20* (2006.01)
*C07H 21/02* (2006.01)

(52) U.S. Cl.
USPC .. 435/135; 435/91.1; 435/320.1; 435/252.33; 536/23.1; 536/23.2

(58) Field of Classification Search
USPC ........ 435/135, 91.1, 320.1, 252.33; 536/23.1, 536/23.2
See application file for complete search history.

(56) References Cited

PUBLICATIONS

Chien et al., Effects of different substrate composition on biosynthesis of polyhydroxybutyrate-co-hydroxyvalerate by recombinant *Escherichia coli*. Appl Biochem Biotechnol., 2012, vol. 166: 796-804.*
Horng et al., Enhanced polyhydroxybutyrate (PHB) production via the coexpressed phaCAB and vgb genes controlled by arabinose PBAD promoter in *Escherichia coli*. Lett. Appl. Microbiol., 2010, vol. 50: 158-167.*
Liu et al., Biosynthesis of poly(3-hydroxybutyrate-co-3-hydroxyvalerate) by recombinant *Escherichia coli* harboring propionyl-CoA synthase gene (prpE) or propionate permease gene (prpP). Biochem. Engineering J., 2009, vol. 43: 72-77.*

* cited by examiner

*Primary Examiner* — Ganapathirama Raghu
(74) *Attorney, Agent, or Firm* — WPAT, P.C.; Anthony King

(57) ABSTRACT

The invention discloses a method for production of polyhydroxybutyrate-co-polyhydroxyvalerate (PHBV) by recombinant *Escherichia coli* harboring plasmid containing both phaCAB and prpE. Different percentage of hydroxyvalerate can be obtained from the recombinant *E. coli* when cultivated in the medium containing different concentrations of propionic acid. In this patent, we provide a method that integrated all of the genes (i.e. phaCAB, vgb and prpE) required for PHBV production into a single plasmid. The plasmids were then transformed into an *E. coli* host. Results showed that PHBV can be produced by this recombinant *E. coli*, and the ration of HV to HB in the co-polymers can be regulated by addition of different concentrations of propionic acid in the medium. The percentage of HV in the co-polymers can be adjusted from about 3% up to more than 35%.

8 Claims, 3 Drawing Sheets

METHOD TO PRODUCE PHBV BY RECOMBINANT ESCHERICHIA COLI

BACKGROUND OF THE INVENTION

1. Field of the Invention

The present invention is related to a method to produce poly 3-hydroxybutyrate-co-3-hydroxyvalerate (PHBV) by the recombinant *Escherichia coli*, in particular, overexpression of phaCAB-vgb-prpE gene by the recombinant *Escherichia coli* to produce PHBV.

2. Description of the Prior Art

Polyhydroxyalkanoates (PHAs) are high molecular weight polymers that can be used as biopolymers, and are biocompatible, absorbable, and biodegradable. PHAs can also be used as biomedical materials, e.g. implants, films or suturing materials. The monomers of PHAs, HA, are linked by ester bonds. A methyl or ethyl group in its C3 position will result in the formation of polyhydroxybutyrate (PHB) or polyhydroxyvalerate (PHV), respectively, whereas polymerization both of PHB and PHV gives rise to poly 3-hydroxybutyrate-co-3-hydroxyvalerate (PHBV) with the structural form

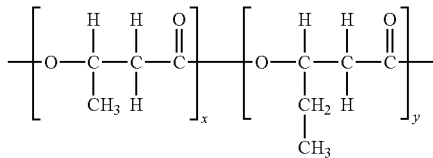

PHBV can be used as biodegradable plastics. Due to its extraordinary biocompatibility and thermoplasticity, at present, PHBV is broadly used to produce various types of PHBV films for medical or pharmaceutical use, drug capsules, bone filler, or surgical stitches.

It was known that *Ralstonia eutropha* can import large amounts of propionate into cells by using propionate permease (PrpP) and can synthesize propionyl CoA from propionate by using propionyl-CoA synthetase (PrpE); hence, the addition of propionate in the bacteria culture medium can induce the formation of 3-ketovaleryl-CoA by facilitating the reaction between propionyl-CoA and acetyl-CoA using pre-existed Beta-ketothiolase B (BktB), which consequently resulted in hydroxyvalerate (HV) after the process of reduction catalyzing by the reductase, and said HV can react with hydroxybutyrate (HB) to form PHBV.

Various properties of PHBV including tensile strength, elastic modulus, and crystallinity will decrease accordingly with increased HV amount, while its elasticity and flexibility will notably improved. However, the amount of PHBV synthesized by bacteria in nature is usually very low (less than 5%). In the case of using wild strains in culture medium with propionate to produce PHBV, the growth of most microorganisms will be inhibited which consequently restricts the yield and the availability of the product. Previous studies have demonstrated co-transformed of *E. coli* with plasmids which one carries phaCAB gene (for PHB synthesis) and the other carries bktB, prpP or prpE gene (relevant genes involved in the metabolism of propionate); yet, culturing of the resulted recombinant *E. coli* requires two different antibiotics in the growth medium which results in the cost rise and the cost is a major concern in practical production. Furthermore, the numbers and ratios of the two plasmids in *E. coli* cannot be controlled, and the amount of HV produced by the recombinant *E. coli* was only 15~20% (mol %) of total PHBV.

The transformed recombinant *E. coli* containing only one plasmid carries both phaCAB and prpE genes disclosed in present invention. Also, the amount of HV in total PHBV produced by the recombinant *E. coli* strain disclosed in the present invention is regulated by the concentration of propionate in the culture medium, and is around 35%. Thus, the method to produce PHBV by microorganisms disclosed in the present invention has clearly demonstrated the significant improvements.

SUMMARY OF THE INVENTION

The present invention features a method to produce PHBV by constructing a strain of recombinant *Escherichia coli* carrying both phaCAB and prpE genes.

In one aspect, the invention is to provide a method to produce PHBV containing different ratios of HV (5%~0.35%) by regulating the concentration of propionate in an *Escherichia coli* culture medium.

In the other aspect, the invention is to provide PHBV containing high percentage of HV.

The present invention discloses a method to produce PHBV by a recombinant *Escherichia coli* carrying both phaCAB and prpE genes comprising of the following steps:
(1) Providing a DNA construct (i.e. a plasmid) carrying phaCAB-vgb-prpE gene;
(2) providing a *Escherichia coli* strain;
(3) transforming of the *Escherichia coli* with the DNA construct;
(4) screening and culturing the recombinant *Escherichia coli*, and
(5) harvesting the recombinant *Escherichia coli* and producing PHBV by further purification.

The cloned prpE gene is inserted into the plasmid carrying vgb-phaCAB gene, and forms a DNA construct carrying phaCAB-vgb-prpE gene, in which phaCAB encodes PHB synthase, prpE encodes propionyl-Co A synthetase, and vgb encodes *Vitreoscilla* Hemoglobin (VHb) which is helpful in production of PHB in *E. coli*. Next, the transformation of the *Escherichia coli* with the said DNA construct, in which the *Escherichia coli* strain is, but is not limited to, DH5α. After screening, the recombinant *Escherichia coli* is named CT-2E, and the MR medium containing propionate or sodium propionate was inoculated with CT-2E to produce PHBV.

DETAILED DESCRIPTION OF THE PREFERRED EMBODIMENT

Example 1

Construction of pBHB-2-prpE Plasmids Carrying phaCAB and prpE

Figure 1:
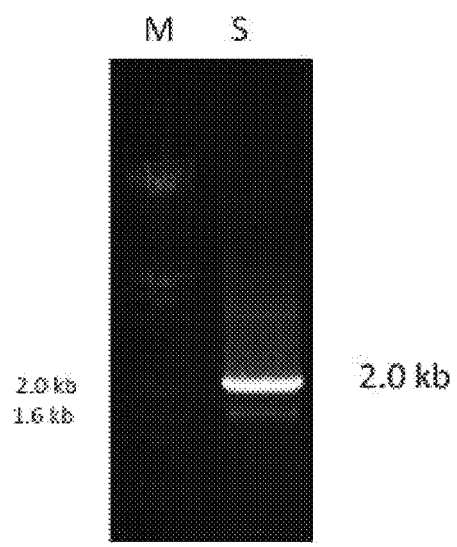
FIG. 1 is the electrophoresis results of PCR products of *Salmonella enterica* prpE.
(M: marker; S: *Salmonella enterica*)
FIG. 2 describes the schematic diagram of the construction steps of pBHB-2-prpE.

Cloning of prpE Gene
Specific primers for prpE gene were designed based on the nucleotide sequence of *Salmonella enterica* published by National Center for Biotechnology Information (NCBI), and contains HindIII restriction enzyme sites at both ends. *Salmonella enterica* chromosomal DNA was used as the template for PCR and prpE gene fragment and was obtained by using DNA extraction kit (VIOGENE) after further purification. The prpE PCR product is 1887 bps (FIG. 1), and following ligation with pGEM-T easy vector, the construct was transformed into competent cells. Plates containing X-gal, IPTG, and ampicillin were used for blue-white screening, and the white colonies were selected and further cultured for 12 hours. The plasmid DNA was then extracted, and the extracted plasmid DNA was digested with the restriction enzyme, HindIII, for confirmation.

2. Construction Steps of the Plasmid Carrying prpE and phaCAB Genes.

Figure 2:
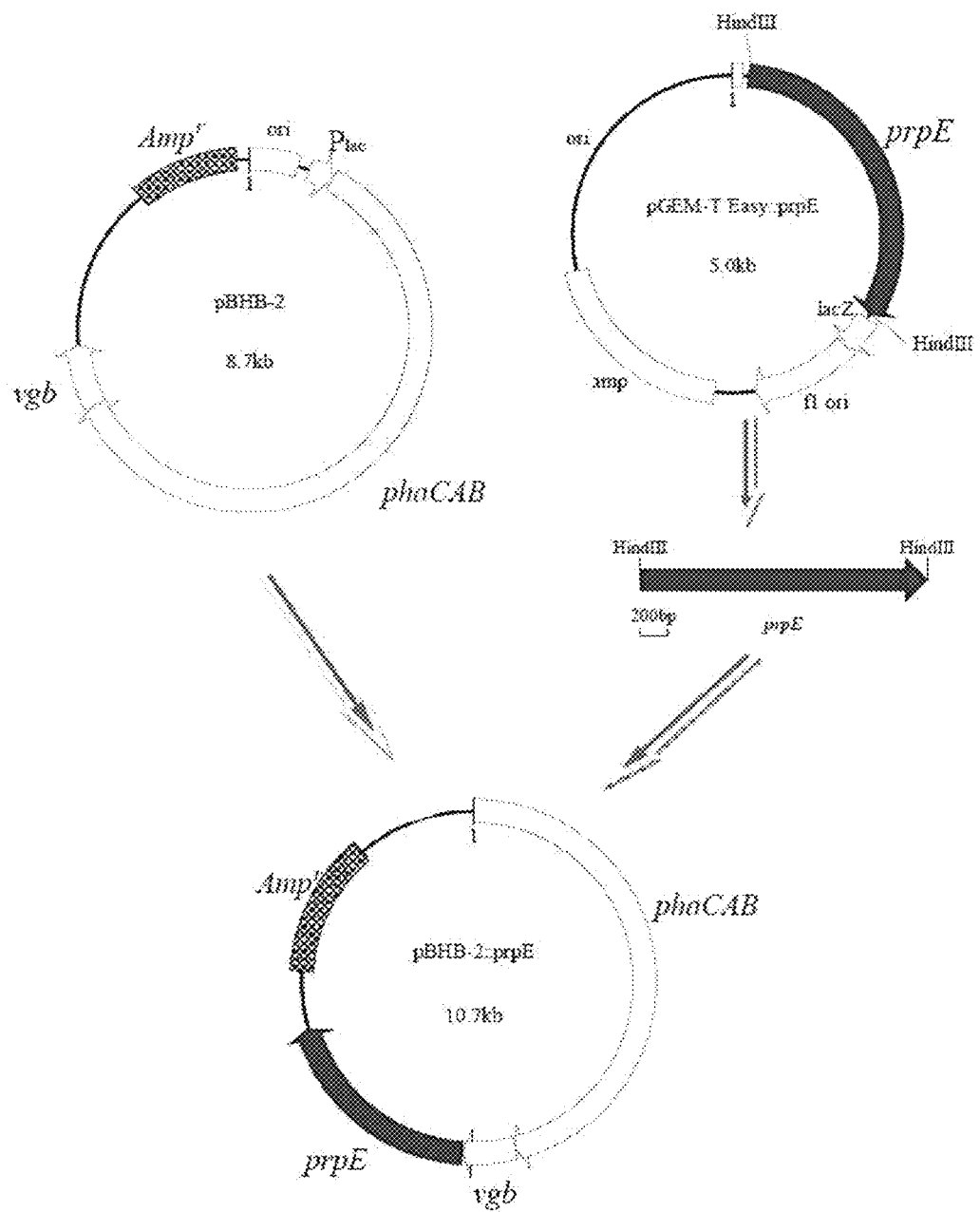
Figure 3:
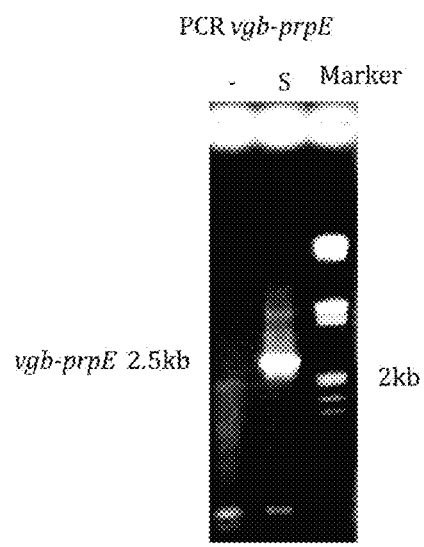
FIG. 3 is the electrophoresis results of PCR products of vgb-prpE of pBHB-2-prpE.
(M: marker; S: pBHB-2-prpE; -: pBHB-2)
Figure 4:
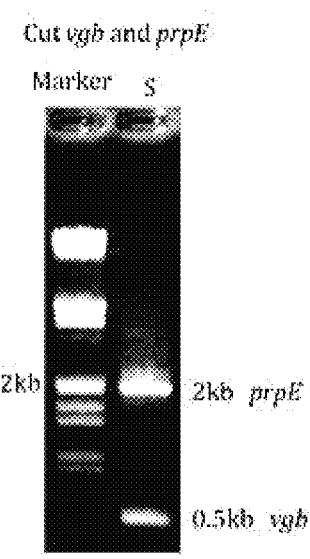
FIG. 4 is the electrophoresis results of HindIII digestion of vgb-prpE PCR product.
(M: marker; S: pBHB-2-prpE)

Excised prpE gene from pGEM-T Easy-prpE using HindIII, extraction of the DNA fragment which is around 2 kb from agarose gel electrophoresis, and digested pBHB-2 plasmid carrying phaCA gene with HindIII and extracted the 8.7 kb DNA fragment from agarose gel electrophoresis. Ligation of the two fragments from the above resulted in the plasmid pBHB-2-prpE (named pBHB-2E), and the detailed schematic diagram is shown in FIG. 2. Transformation of *E. coli* strain DH5α with pBHB-2E, and stored at −70° C. To confirm whether the prpE, and its upstream genes and transcription start sites were in cis direction, forward primer (vgb-F) for prpE upstream gene, vgb, and reverse primer (prpE-R) for prpE in pBHB-2E were used for PCR reaction. The presence of PCR product of vgb-prpE indicated all the above genes are in cis; otherwise, no PCR product would be found (FIG. 3). The obtained PCR product was further digested with HindIII which resulted in two fragments: 2.0 kb prpE and 0.5 kb vgb (FIG. 4).

Example 2

The Effects of Overexpressing prpE on PHBV Accumulation

To examine whether overexpression of prpE could increase the percentage of hydroxyvalerate (HV) in poly 3-hydroxybutyrate-co-3-hydroxyvalerate (PHBV) as expected, *E. coli* strain XL1-Blue was transformed with pBHB-2E, and renamed as CT-2E. Compared the control *E. coli* strain (CT-2) transformed with vector without prpE by using Gas Chromatography (GC) for product analysis to further investigate the effects of overexpressing prpE on HV productivity. Transformed *E. coli* strains were cultured in LB broth for 12 hours and then inoculated into the culture medium in the ratio of 1%. The bacteria liquid was collected and centrifuged 48 hours later, and was subjected to GC analysis after drying. The average of multiple experiment results were calculated using calibration curve and the results are shown in Table 1. According to the results of optical density at 600 nm (OD600) and cell dry weight (CDW) of CT-2E and CT-2, the overexpression of prpE inhibited the growth of CT-2E when compared to CT-2, and the OD600 value, CDW, and PHBV production of CT-2E decreased about 4.62%, 16.28%, and 15.70%, respectively. However, the percentage of HV in PHBV produced increased significantly, about 22.81% of each gram of PHBV produced is HV. The conversion rate of propionate to HV was 72.48%, which indicated that in spite of growth inhibition, overexpression of prpE in *E. coli* can dramatically increase the usage of propionate and can help to accumulate significant amount of HV.

TABLE 1

Comparison of growth conditions and PHBV productivity between CT-2 and CT-2E

| Strain | CT-2 | CT-2E |
|---|---|---|
| plasmid | pBHB-2 | pBHB-2-prpE |
| $OD_{600}$ | 27.98 | 26.68 |
| CDW(g/L) | 6.8 | 5.7 |
| PHA/CDW(w/w) | 58.71% | 43.01% |
| PHV/PHA(w/w) | 4.62% | 22.81% |
| Conversion rate (propionate to PHV) | 23.91% | 72.48% |

Example 3

The Effects of Propionate at Different Concentrations on PHBV Production

Further exploration, the effects of the added 0~48 mM propionate on PHBV production. CT-2E, pre-cultured for 12 hours with an initial OD600 at 0.05, was sub-cultured in the MR growth medium containing 2% glucose and 1.5% yeast extract (initial pH is 6.5) at 30° C., 200 rpm. As shown in Table 2, the amount of HV increased accordingly with the concentration of propionate; yet, the amount of HV and CDW declined when the concentration of propionate was at 48 mM. The reason of the cell growth arrest might be caused by the high concentration of propionate which subsequently affected the synthesis of PHBV. Based on these results, the optimal concentration of propionate is 32 mM, and under this condition, CDW and the concentration of PHA are 11.25 and 5.15 g/L, respectively; and the amounts of HB and HV are 34.14% and 11.06%, respectively.

TABLE 2

The effects of propionate at different concentrations on cell dry weight and production of PHBV.

| Propionate Concentration (mM) | PHBV percentage (%) | PHB percentage (%) | PHV percentage (%) | Cell dry weight (g/L) | HV Concentration (g/L) | HB Concentration (g/L) | PHBV Concentration (g/L) | HV/PHBV (%) |
|---|---|---|---|---|---|---|---|---|
| 0 | 55.86 | 55.86 | 0.00 | 9.25 | 0.00 | 5.17 | 5.17 | 0.00 |
| 8 | 49.41 | 48.20 | 1.21 | 11.38 | 0.14 | 5.48 | 5.62 | 2.46 |
| 16 | 45.19 | 40.56 | 4.62 | 12.50 | 0.58 | 5.07 | 5.65 | 10.23 |
| 24 | 45.63 | 37.03 | 8.60 | 11.38 | 0.98 | 4.21 | 5.19 | 18.85 |
| 32 | 45.74 | 34.14 | 11.60 | 11.25 | 1.30 | 3.84 | 5.15 | 25.36 |
| 48 | 31.95 | 20.92 | 11.03 | 8.5 | 0.94 | 1.78 | 2.72 | 34.51 |

Example 4

The Effects of Different Concentrations of Sodium Propionate on Production of PHBV Explore the effects of sodium propionate at different concentrations on recombinant strain, CT-2E. The concentrations of sodium propionate are between 0-48 mM, and according to Table 3, the amount of HV increased along with the concentrations of sodium propionate. On the other hand, cell growth arrest was observed while the concentration of sodium propionate was increased; moreover, the final cell dry weight was between 9.25~10.38 g/L. According to the results, the amount of HV increased up to 5% when the concentration of sodium propionate reached 32 mM. Furthermore, PHBV production in the presence of propionate and sodium propionate was compared, and the results are shown in Table 3, addition of propionate can result in higher HV concentrations.

TABLE 3

The effects of sodium propionate at different concentrations on cell dry weight and PHA production

| sodium propionate Concentration (mM) | PHBV percentage (%) | HB percentage (%) | HV percentage (%) | Cell dry weight (g/L) | HV Concentration (g/L) | HB Concentration (g/L) | PHBV Concentration (g/L) | HV/PHBV (%) |
|---|---|---|---|---|---|---|---|---|
| 0 | 39.22 | 39.22 | 0.00 | 10 | 0.00 | 3.92 | 3.92 | 0.00 |
| 16 | 43.35 | 39.90 | 3.45 | 10.38 | 0.36 | 4.14 | 4.50 | 7.96 |
| 32 | 44.67 | 34.16 | 10.51 | 10 | 1.05 | 3.42 | 4.47 | 23.54 |
| 48 | 45.29 | 29.85 | 15.45 | 9.25 | 1.43 | 2.76 | 4.19 | 34.10 |

What is claimed is:

1. A method for producing poly 3-hydroxybutyrate-co-3-hydroxyvalerate by construction of a recombinant *Escherichia coli* carrying phaCAB of *Ralstonia eutropha*, wherein phaCAB is polyhydroxyalkanoates biosynthesis operon and propionyl-CoA synthase (prpE) genes of *Salmonella enterica* comprising the steps of:
   (a) Providing a DNA construct carrying phaCAB-vgb-prpE genes, wherein vgb is *Vitreoscilla* globin gene from *Vitreoscilla stercoraria*;
   (b) Providing an *Escherichia coli* strain;
   (c) Transforming the DNA construct into the *Escherichia coli* strain;
   (d) Screening and culturing the recombinant *Escherichia coli*;
   (e) Harvesting the recombinant *Escherichia coli* and producing poly 3-hydroxybutyrate-co-3-hydroxyvalerate by further purification;
   the prpE DNA fragment is ligated into the plasmid carrying phaCAB gene in cis, wherein the phaCAB gene encodes polyhydroxyvalerate synthase having the nucleotide sequence of SEQ ID NO: 1, and forms a DNA construct carrying phaCAB-vgb-prpE genes, which is subsequently transformed into the *Escherichia coli*; following screening, the recombinant *Escherichia coli* is cultured in the medium for expression of poly 3-hydroxybutyrate-co-3-hydroxyvalerate.

2. The method of claim 1, wherein the *Escherichia coli* strain is DH5α.

3. The method of claim 1, wherein vgb gene in the phaCAB-vgb-prpE DNA construct encodes *Vitreoscilla* Hemoglobin.

4. The method of claim 1, wherein prpE in the phaCAB-vgb-prpE DNA construct encodes propionyl coenzyme A synthetase.

5. The method of claim 1, wherein phaCAB, vgb and prpE genes are all cloned into the same plasmid.

6. The method of claim 1 or claim 5, wherein the plasmid carrying phaCAB, vgb, and prpE genes also carries a ampicillin-resistance gene.

7. The method of claim 1, wherein the culture medium used is minimum requirements medium (MR medium) comprising different concentrations of propionate or sodium propionate.

8. The method of claim 7, wherein the MR medium is consisting of 2% glucose and 1.5% yeast extract.

* * * * *

SEQUENCE LISTING

<160> NUMBER OF SEQ ID NOS: 1

<210> SEQ ID NO 1
<211> LENGTH: 8966
<212> TYPE: DNA
<213> ORGANISM: Ralstonia eutropha

<400> SEQUENCE: 1

```
atttccgcac gctggccacg gtgccgctgg ggcggggctt cgtgtcgatg gtgatgtgca      60
agctggagac cggccgcacg caccagatcc gcgtgcattt cgagtcgatc ggccacccgc     120
tggtgggcga cccggcctac ttccgcgcca cgcagcgcgg cagcgcccg gcggtccgcg     180 caccgctgcc ggtgccgtat gagcgccagg cgctgcatgc gtaccagctc ggcctggtgc     240
atccggccac cggcaagcgc atgtcgtgga ccgcgcagcc gccgcaagac ctgcaggcgc     300
tgatcgatgc gctggatttt gaaagcgcgc aggccgacga ggatgaagaa ggctgggacg     360
aagtctggga aggcggcgag gcccactggg aatacgctgg tgatgacgag gacgacgatg     420
acgatgagcg cagcgcctga tcgcgcctgg ctggtccctg actggcccgc gccggcgcgt     480
gtgcgcgcgt tgtcaaccac gcgccaggc ggtgtcagca agggcccgta cgggcttgcc     540
ggcggcgccc ccggcggcct gaacctgggc acccacgttg gcgacgacgc cgccgacgtg     600
gcgcgcaacc gcgcgcggct ggccgcctgc ctgccgtcga tgccgcaatg gctggagcag     660
gtgcatggct gcgcggtcgc cacggtcgac catgtggcgg ccccgggcgc gcccgtgccc     720
caggccgacg cgagcctggc ggtggtaccc ggccaagtct cgcgcgtgat gacggcggat     780
tgcctgccgg tgctgctatg cgatgcgcag gggacggtgg tgggcgccgc gcatgcgggc     840 tggcgcgcc tgtgcagcgg cgtgatcgaa gccacgctgt cacggatgca ggccgctgcc     900
ggtgccgcgc gctggctggc atggctgggc ccggccatcg gccccgatgc gttcgaggtg     960
ggtgccgaag tgcgcgatgc cttcctgcc caggcacgcg ccgatgaaca ggtcgcggtt    1020
gccgcagcct tccgccctgg tgccccgggc aagtaccttg ccgacatcta tgcgctggcg    1080
cgcacgcgcc tggcgcgcgc cggctgtacc gaggtctacg gcggcgacgc ctgcaccgtg    1140
gccgacgccg gtcgcttcta ctcctatcgg cgcgatggcg tgaccggccg catggccagc    1200
ctggtctggc tggcggactg agcccgccgc tgcctcactc gtccttgccc ctggccgcct    1260
gcgcgcgctc ggcttcagcc ttgcgtcggc ggcggccggg cgtgcccatg atgtagagca    1320
ccagcgccac cggcgccatg ccatacatca ggaaggtggc aacgcctgcc accacgttgt    1380
gctcggtgat cgccatcatc agcgccacgt agagccagcc aatggccacg atgtacatca    1440
```

```
aaaattcatc cttctcgcct atgctctggg gcctcggcag atgcgagcgc tgcataccgt    1500
ccggtaggtc gggaagcgtg cagtgccgag gcggattccc gcattgacag cgcgtgcgtt    1560
gcaaggcaac aatggactca aatgtctcgg aatcgctgac gattcccagg tttctccggc    1620
aagcatagcg catggcgtct ccatgcgaga atgtcgcgct tgccggataa aaggggagcc    1680
gctatcggaa tggacgcaag ccacggccgc agcaggtgcg gtcgagggct tccagccagt    1740
tccagggcag atgtgccggc agaccctccc gctttggggg aggcgcaagc cgggtccatt    1800
cggatagcat ctccccatgc aaagtgccgg ccagggcaat gcccggagcc ggttcgaata    1860
gtgacggcag agagacaatc aaatcatggc gaccggcaaa ggcgcggcag cttccacgca    1920
ggaaggcaag tcccaaccat tcaaggtcac gccggggcca ttcgatccag ccacatggct    1980
ggaatggtcc cgccagtggc agggcactga aggcaacggc cacgcggccg cgtccggcat    2040
tccgggcctg gatgcgctgg caggcgtcaa gatcgcgccg gcgcagctgg gtgatatcca    2100
gcagcgctac atgaaggact ctcagcgct gtggcaggcc atggccgagg caaggccga    2160 ggccaccggt ccgctgcacg accggcgctt cgccggcgac gcatggcgca ccaacctccc    2220
atatcgcttc gctgccgcgt tctacctgct caatgcgcgc gccttgaccg agctggccga    2280
tgccgtcgag gccgatgcca agacccgcca gcgcatccgc ttcgcgatct cgcaatgggt    2340
cgatgcgatg tcgcccgcca acttccttgc caccaatccc gaggcgcagc gcctgctgat    2400
cgagtcgggc ggcgaatcgc tgcgtgccgg cgtgcgcaac atgatggaag acctgacacg    2460
cggcaagatc tcgcagaccg acgagagcgc gtttgaggtc ggccgcaatg tcgcggtgac    2520
cgaaggcgcc gtggtcttcg agaacgagta cttccagctg ttgcagtaca agccgctgac    2580
cgacaaggtg cacgcgcgcc cgctgctgat ggtgccgccg tgcatcaaca agtactacat    2640
cctggacctg cagccggaga gctcgctggt gcgccatgtg gtggagcagg acatacggt    2700 gtttctggtg tcgtggcgca atccggacgc cagcatggcc ggcagcacct gggacgacta    2760
catcgagcac gcggccatcc gcgccatcga agtcgcgcgc gacatcagcg ccaggacaa    2820 gatcaacgtg ctcggcttct gcgtgggcgg caccattgtc tcgaccgcgc tggcggtgct    2880
ggccgcgcgc ggcgagcacc cggccgccag cgtcacgctg ctgaccacgc tgctggactt    2940
tgccgacacg ggcatcctcg acgtctttgt cgacgagggc catgtgcagt gcgcgaggc    3000 cacgctgggc ggcggcgccg gcgcgccgtg cgcgctgctg cgcggccttg agctggccaa    3060
taccttctcg ttcttgcgcc cgaacgacct ggtgtggaac tacgtggtcg acaactacct    3120
gaagggcaac acgccggtgc cgttcgacct gctgttctgg aacggcgacg ccaccaacct    3180
gccggggccg tggtactgct ggtacctgcg ccacacctac ctgcagaacg agctcaaggt    3240
accgggcaag ctgaccgtgt gcggcgtgcc ggtggacctg ccagcatcg acgtgccgac    3300 ctatatctac ggctcgcgcg aagaccatat cgtgccgtgg accgcggcct atgcctcgac    3360
cgcgctgctg gcgaacaagc tgcgcttcgt gctgggtgcg tcgggccata tcgccggtgt    3420
gatcaacccg ccggccaaga acaagcgcag ccactggact aacgatgcgc tgccggagtc    3480
gccgcagcaa tggctggccg gcgccatcga gcatcacggc agctggtggc cggactggac    3540
cgcatggctg ccgggcagg ccggcgcgaa acgcgccgcg cccgccaact atggcaatgc    3600
gcgctatcgc gcaatcgaac ccgcgcctgg gcgatacgtc aaagccaagg catgacgctt    3660
gcatgagtgc cggcgtgcgt catgcacggc gccggcaggc ctgcaggttc cctcccgttt    3720
ccattgaaag gactacacaa tgactgacgt tgtcatcgta tccgccgccc gcaccgcggt    3780
```

-continued

```
cggcaagttt ggcggctcgc tggccaagat cccggcaccg gaactgggtg ccgtggtcat    3840
caaggccgcg ctggagcgcg ccggcgtcaa gccggagcag gtgagcgaag tcatcatggg    3900
ccaggtgctg accgccggtt cgggccagaa ccccgcacgc caggccgcga tcaaggccgg    3960
cctgccggcg atggtgccgg ccatgaccat caacaaggtg tgcggctcgg gcctgaaggc    4020
cgtgatgctg gccgccaacg cgatcatggc gggcgacgcc gagatcgtgg tggccggcgg    4080
ccaggaaaac atgagcgccg ccccgcacgt gctgccgggc tcgcgcgatg gtttccgcat    4140
gggcgatgcc aagctggtcg acaccatgat cgtcgacggc ctgtgggacg tgtacaacca    4200
gtaccacatg ggcatcaccg ccgagaacgt ggccaaggaa tacggcatca cacgcgaggc    4260
gcaggatgag ttcgccgtcg gctcgcagaa caaggccgaa gccgcgcaga aggccggcaa    4320
gtttgacgaa gagatcgtcc cggtgctgat cccgcagcgc aagggcgacc cggtggcctt    4380
caagaccgac gagttcgtgc gccagggcgc cacgctggac agcatgtccg gcctcaagcc    4440
cgccttcgac aaggcggca cggtgaccgc ggccaacgcc tcgggcctga acgacggcgc    4500
cgccgcggtg gtggtgatgt cggcggccaa ggccaaggaa ctgggcctga cccgctggc    4560
cacgatcaag agctatgcca acgccggtgt cgatcccaag gtgatgggca tgggcccggt    4620
gccggcctcc aagcgcgccc tgtcgcgcgc cgagtggacc ccgcaagacc tggacctgat    4680
ggagatcaac gaggcctttg ccgcgcaggc gctggcggtg caccagcaga tgggctggga    4740
cacctccaag gtcaatgtga acggcggcgc catcgccatc ggccacccga tcggcgcgtc    4800
gggctgccgt atcctggtga cgctgctgca cgagatgaag cgccgtgacg cgaagaaggg    4860
cctggcctcg ctgtgcatcg gcggcggcat gggcgtggcg ctggcagtcg agcgcaaata    4920
aggaaggggt tttccggggc cgcgcgcggt tggcgcggac ccggcgacga taacgaagcc    4980
aatcaaggag tggacatgac tcagcgcatt gcgtatgtga ccggcggcat gggtggtatc    5040
ggaaccgcca tttgccagcg gctggccaag gatggctttc gtgtggtggc cggttgcggc    5100
cccaactcgc cgcgccgcga aaagtggctg gagcagcaga aggccctggg cttcgattc    5160
attgcctcgg aaggcaatgt ggctgactgg gactcgacca agaccgcatt cgacaaggtc    5220
aagtccgagg tcgcgaggt tgatgtgctg atcaacaacg ccggtatcac ccgcgacgtg    5280
gtgttccgca agatgacccg cgccgactgg gatgcggtga tcgacaccaa cctgacctcg    5340
ctgttcaacg tcaccaagca ggtgatcgac ggcatggccg accgtggctg gggccgcatc    5400
gtcaacatct cgtcggtgaa cgggcagaag ggccagttcg ccagaccaa ctactccacc    5460
gccaaggccg gcctgcatgg cttcaccatg gcactggcgc aggaagtggc gaccaagggc    5520
gtgaccgtca acacggtctc tccgggctat atcgccaccg acatggtcaa ggcgatccgc    5580
caggacgtgc tcgacaagat cgtcgcgacg atcccggtca agcgcctggg cctgccggaa    5640
gagatcgcct cgatctgcgc ctggttgtcg tcggaggagt ccggtttctc gaccggcgcc    5700
gacttctcgc tcaacggcgg cctgcatatg ggctgacctg ccggcctggt tcaaccagtc    5760
ggcagccggc gctggcgccc gcgtattgcg gtgcagccag cgcggcgcac aaggcggcgg    5820
gcgtttcgtt tcgccgcccg tttgcgggc cgtcaaggcc cgcgaatcgt ttctgcccgc    5880
gcggcattcc tcgcttttg cgccaattca ccgggttttc cttaagcccc gtcgcttttc    5940
ttagtgcctt gttgggcata gaatcagggc agcggcgcag ccagcaccat gttcgtgcag    6000
cgcggccctc gcggggcga ggctgcaggc cgccacgcgc agccatgcgc gaacgggcca    6060
ccagatggcc ggcacgacaa caagcagatg gcgcgggcga taccgatttg cgcactgcac    6120
cccatgcggt gcagcagcgc gcaaacagcg atgacacaag gacagagcac cgatggccac    6180
```

-continued

```
gaccaaaaaa ggcgcagagc gactgatcaa aaagtatccg aaccgtaggc tctacgacac    6240
ccagaccagc acctacatca ccctggccga cgtcaagcag ctggtcatgg attcagaaga    6300
attcaaggtc gtcgacgcca agtctggtga cgaactgacc cgcagcatct tgctgcagat    6360
catcctggaa gaagaaacgg gcggcgtgcc gatgttctcc agcgcgatgc tgtcgcagat    6420
catccgcttc tacggccatg ccatgcaggg catgatgggc acctacctgg aaaagaacat    6480
ccaggccttc atcgacatcc agaacaagct ggccgagaac tccaagggcc tgtattccgg    6540
cgaaaccttc agccccgaca tgtggtcgca gttcatgaac atgcagggcc gatgatgca    6600 gggcatgatg agcaactaca tcgagcagag caagaacctg ttcgtgcaga tgcaggagca    6660
gatgcaaagc caggccaaaa atatgttcgg acgttcccg ttcaaccagc cggacaagaa     6720
gtaagacact ggcagcggcg ggcgctacac ccgccgcata tcccgcacgc tggctggcac    6780
tcagccagcg ctcgcatgca ggcggatgcc cagcgcccgc atcaccttcc agatcgtccc    6840
gaactccgga ttgccttcgc ctgagagcga gcggtagagg cttccgcgcg aaaggcccgt     6900
ttcgcgggcc agtcgcgtca tgccgcgcgc acgcgccacc accccgagtg cgtaggcaat    6960
gaatcgatcg tcgtcgccgg cctcggccag gcaggcatcc aggtaggcgg cgatctcctg    7020
atcgttcctc agatgctcgg cggagtccca ggggcgggtt ggttccttca tggctcactc    7080
cagatcaaga ttggccgcca gactgcgtgc tctttcgata tcagcgtgct gggtcgactt    7140
gttgcctccg cagagcagga tcacaattac ctggccgcgt tgctgaaagt agatgcggta    7200
gcccgggccg tggtccacgc gcatttcgct gactccaccg ccaagggctt tagcgtcgcc    7260
gggattcccg ttcagtaagc ggtcgacgcg gacctggatg cgaatcctgg cgacgtggtc    7320
gcgcaaggcc gaataccagc ggtcggaaat ttggttgtc cggatgctga gcatacctta     7380
ccgtagcctg tgggctacgg taagagaatc gccgatccct gaaaaccgtg ctgatgcaaa    7440
gcaggtagaa tgcgcggtct gcgtccccgg gcgcacgcaa tcacgcaact ctctccagcg    7500
gcggctcagt gtggactcgc cttttgtgcg cgaaaaccca tgccctccgt tatccaatat    7560
gctcgtccgc cccttaaggc ccggctctct gcttcgatga aggcttcgcc atgagccggc    7620
tgttcctggc ccccatggaa gggcttgccg actacgtctt gcgcgacgtg ctgaccgaca    7680
ctggcggcta cgacggctgt gtgtccgagt tcgtccgggt gaccggttcg ttgcttcccg    7740
cccgcgtcta cgagcgcgaa acgcccgaaa tcctcgccgg cggctatacc cgcagcggca    7800
cgccgatggt gatccagttg ctcggcagcg atccggaatg gctggcgcgc aatgccgcct    7860
atgccgcgac cttgtcgccg catggcatcg acctgaactt cggctgcccc gccaaggtcg    7920
tcaaccggca tggcggcggt gccatgctgc tgacgaatcc tgagttgttg aaccggatcg    7980
tcgcgtccgt gcgcgcggcg gtgccggccc atatcgccgt gacggcaaaa atgcggctgg    8040
gcgtttccga tgcctcgctg gccattgatt gcgccacggc gctggccgaa ggcggcgcgg    8100
cttcgctcgt cgtgcatgcc cggacgcggg accatggcta ccggccgccg gcccactggg    8160
actggatcgc gcgcattgcg gcggcggtgg acgtgccggt gattgccaac ggagatgtct    8220
ggaccgtcgc cgactgggag cgttgccggg ccgtcagcgg ttgcgccgac gtgatgatcg    8280
ggcgcggcgc cgtgtccgat cctttcctgg ccttgcgcat tcgcgggctg atggacggtt    8340
cgccgtcgga ccaggagtgg ccgctggtgc tgcgccagat cgccacctac ctgaaaaagc    8400
tgcatgcccg tatcgcgtcg tgccatgagc atgggcgcgt gaaactgtgg ctcagctatc    8460
tcaagcggac ctggccacag gccgccgaac tgcatgcggc catccggcgc atgcaggact    8520
```

-continued

```
cgctggagat agagcgggtc ctggaaggcc tgccgggagc cgcgaccgcg ccggaatgac    8580
gcagcctggg ccacatgtat ggtgtcaggc gccgagaatt catggcaaac ggttaaaatg    8640
cgcgattggc tcaccggctg ccggccttgt ccccgcatat tcgccgcgcc cgcccccaca    8700
ttcggattgc actgtgaaaa acccttcaga atcaacgacc cagaaagacc atagtccgcg    8760
tgtgggattc gtttcccttg gctgccccaa ggccctggtc gactccgagc agatcatcac    8820
ccagctgcgc gccgagggct atgccatcag cggcacctat gacggcgctg acctggtcgt    8880
ggtcaatacc tgcggcttta tcgacgaggc cgtgcaggag agcctggacg ccatcggcga    8940
ggccctgacc gagaacggca aggtca                                          8966
```